United States Patent [19]

Sessions

[11] Patent Number: 4,679,564
[45] Date of Patent: Jul. 14, 1987

[54] MONITORING ELECTRODE ATTACHABLE TO A PATIENT

[76] Inventor: Robert W. Sessions, German Church Rd., Hinsdale, Ill. 60521

[21] Appl. No.: 657,588

[22] Filed: Oct. 4, 1984

[51] Int. Cl.⁴ ............................................... A61B 5/04
[52] U.S. Cl. ..................................... 128/640; 128/798
[58] Field of Search ................................. 128/639–641, 128/644, 798, 802, 803

[56] References Cited

U.S. PATENT DOCUMENTS

| | | | |
|---|---|---|---|
| 2,943,638 | 7/1960 | Howell | 137/498 |
| 3,565,059 | 2/1971 | Hauser et al. | 128/640 |
| 3,805,769 | 4/1974 | Sessions | 128/641 |
| 4,040,412 | 8/1977 | Sato | 128/640 |
| 4,102,331 | 7/1978 | Gravzel et al. | 128/640 |
| 4,141,366 | 2/1979 | Cross, Jr. et al. | 128/640 |
| 4,239,046 | 12/1980 | Ong | 128/640 |
| 4,243,051 | 1/1981 | Wittemann | 128/802 X |
| 4,370,984 | 2/1983 | Cartmell | 128/640 |
| 4,391,278 | 7/1983 | Cahalan et al. | 128/640 |
| 4,409,981 | 10/1983 | Lundberg | 128/640 |
| 4,503,860 | 3/1985 | Sams et al. | 128/639 |
| 4,524,087 | 6/1985 | Engel | 128/640 X |

Primary Examiner—William E. Kamm
Assistant Examiner—Angela D. Sykes
Attorney, Agent, or Firm—Leydig, Voit & Mayer

[57] ABSTRACT

A monitoring electrode for attachment to a patient for use with electronic medical diagnostic and monitoring equipment has a laminate construction including a foam pad, a conductor carrier strip having a metallized conductor thereon adjacent to the foam pad, the conductor carrier and a portion of the foam pad being covered by a conductive film, also applied to the foam pad in the form of a strip. The surface of the foam pad and the exposed portion of the conductive film strip to be attached to the patient are covered with an adhesive layer. The foam strip has a recess in the periphery thereof forming a tab onto which the metallized conductor extends, to which a lead of the diagnostic equipment can be attached, such as by a clip.

9 Claims, 5 Drawing Figures

MONITORING ELECTRODE ATTACHABLE TO A PATIENT

BACKGROUND OF THE INVENTION

1. Field of the Invention

The present invention relates to electrodes attachable to a patient, and in particular to such electrodes for use with medical monitoring and diagnostic equipment.

2. Description of the Prior Art

Electrodes in various forms which can be attached to the skin of a patient for providing a means for obtaining various electrical signals from the patient for supply to medical monitoring and diagnostic devices are known in the art. One such electrode is disclosed in U.S. Pat. No. 4,141,366 in the form of a tape with a porous backing material, a conductive layer on one side thereof, covered by a layer of adhesive material.

Another such electrode is disclosed in U.S. Pat. No. 4,102,331 having a foam pad impregnated with conductive gel, and having an adhesive layer for attachment to the skin of a patient. This electrode must be utilized with a separately applied electrically conductive gel. Another electrode is disclosed in U.S. Pat. No. 3,805,769 having self-contained conductive material for providing an electrical connection between the monitoring equipment and the skin of a patient. This electrode must also, however, be utilized with an electrically conductive gel separately applied in a relatively complex ten-step process.

An electrode is disclosed in U.S. Pat. No. 3,565,059 having a normally dry electroconductive material which when wetted with a solvent exhibits adhesive properties for attachment to the skin of a patient. An electrode is disclosed in U.S. Pat. No. 2,943,628 having a laminate construction including a base layer with an adhesive coating on one side and two overlying conductive discs.

The above conventional electrodes exhibit two primary disadvantages, one disadvantage being in the method required to assemble the electrodes, and the other being in the method of applying the electrodes to the patient.

None of the above electrodes can be manufactured from a number of continuous webs of material comprising the different layers which can be continuously fed through an assembly machine in overlying fashion. All of the above conventional electrodes during assembly require one or more stamping or cutting steps, with the subsequent necessity of accurately aligning or superimposing the cut pieces in order to achieve an assembled electrode. The necessity for cutting and subsequent alignment not only complicates the assembly process, but also slows the process in contrast to a continuous feed process.

The second disadvantage of the above electrodes is the necessity for the use of separately-applied conductive gel, or "wet" conductive gel contained within the electrode. The use of separately-applied conductive gel to the area of the patient's skin to which the electrode is to be attached not only adds a step to the attachment of the electrode to the patient, but also requires a supply of such conductive gel always be available. Those electrodes having self-contained wet conductive gel have a limited shelf life before drying out.

SUMMARY OF THE INVENTION

It is an object of the present invention to provide an electrode attachable to a patient for use with electronic medical monitoring and diagnostic equipment which does not require the use of separately-applied or self-contained wet conductive gel.

A further object of the present invention is to provide such an electrode which can be assembled by a series of continuously fed layers applied above one another without the necessity of cutting or stamping.

The above objects are inventively achieved in an electrode of laminate construction including a foam pad, a non-conducting carrier having a metallized conductor strip carried thereon applied to one side of the foam pad, a conductive film strip applied to the same side of the foam pad overlying the carrier and the conductor, and an adhesive layer applied to the side of the faom pad and the exposed conductive film strip for attachment to a patient.

The foam pad has a recess at one side thereof which forms a tab onto which the carrier and the metallized conductor extend, but which is free of the conductive film strip. The tab with the exposed conductor strip thereon is attachable to a lead of the diagnostic or monitoring equipment, such as by a spring clip.

All of the layers comprising the laminate construction of the electrode discloses and claimed herein can be supplied in continuous fashion in strip form or as part of a scored strip in alignment along an axis coincident with the machine direction of the assembly device. Because the strips enter the assembly device already in alignment, there is no need for a separate alignment step in the assembly process, and furthermore no cutting is required during assembly because the component layers are simply placed on top of each other.

DESCRIPTION OF THE PREFERRED EMBODIMENTS

Figure 1:
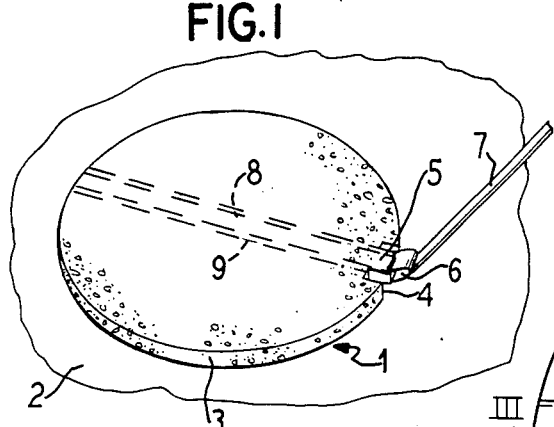
FIG. 1 is a perspective view of an electrode constructed in accordance with the principles of the present invention.

An electrode 1 attachable to a patient is generally referenced at one in FIG. 1. The electrode 1 is shown in place on the skin 2 of a patient for receiving signals from the patient for supply to any suitable electronic medical diagnostic or monitoring device (not shown).

The electrode 1 has a foam pad 3 having a recess 4 at a periphery thereof exposing a tab 5. The tab 5 serves as a means for connecting a lead 7 of the medical diagnostic equipment to the electrode 1, such as by a spring clip 6.

Figure 2:
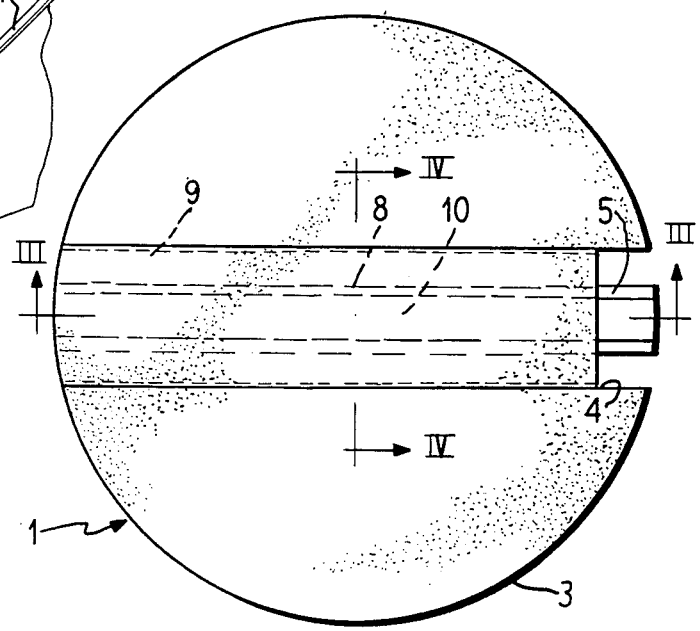
FIG. 2 is a plan view from below of the electrode shown in FIG. 1.

As best seen in FIG. 2, the side of the faom pad 3 of the electrode 1 to be attached to the patient has a non-conductive carrier 8 attached thereto, with a centrally disposed metallized conductive strip 10 on a side thereof facing away from the foam pad 3. The side of the carrier 8 adjacent to the foam pad 3 may have an adhesive thereon for affixing the carrier 8 to the foam pad 3. The carrier 8 may be comprised of any suitable flexible non-conductive material, such as MYLAR. The carrier 8 has a conductor strip 10 on the side thereof facing away from the pad 3 which may consist, for example, of silver. The carrier 8 and the conductive strip thereon extend onto the tab 5.

Figure 3:
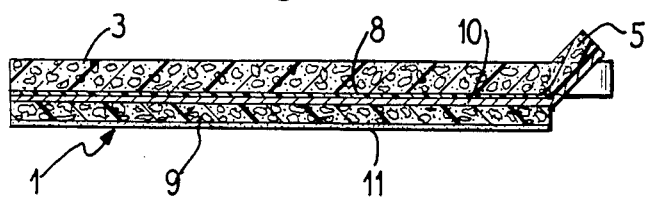
FIG. 3 is a sectional view of the electrode shown in FIG. 2 taken along line III—III.
Figure 4:
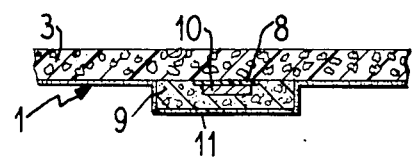
FIG. 4 is a sectional view of a portion of the electrode shown in FIG. 2 taken along line IV—IV.

The carrier 8, and the conductive strip 10 thereon, and portions of the pad 3 on each side of the carrier 8 are covered by a conductive film strip 9. The conductive film strip 9 may be a commercially available product sold under the trade name Kereten. The entire surface of the pad 3 and the exposed portion of the conductive film strip 9 which are to be in contact with the skin 2 of the patient are covered with an adhesive layer 11, as shown in FIGS. 3 and 4. As also shown in FIG. 3, the conductive film strip 9 and the adhesive layer 11 do not extend over the tab 5, so that the conductor 10 is exposed thereon for direct contact with a suitable attachment means for the lead 7 of the device with which the electrode 1 is to be used.

Figure 5:
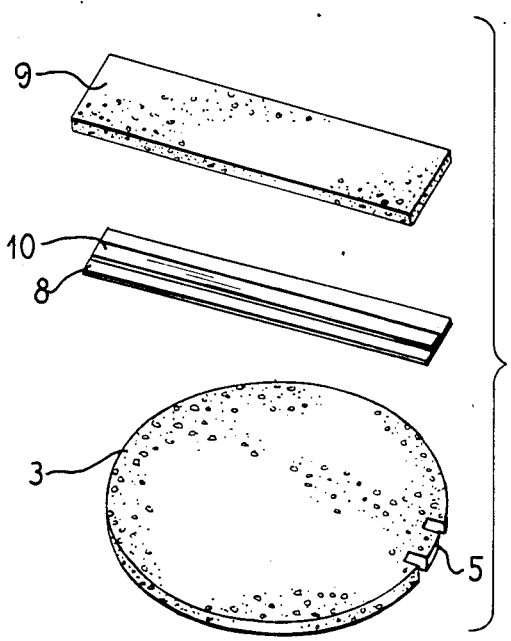
FIG. 5 is an exploded view of the electrode shown in FIG. 1 illustrating the assembly of the layers thereof.

The simplified assembly achieved by the electrode disclosed and claimed herein is shown in FIG. 5, wherein the three layers (with the exception of the adhesive layer) are shown in exploded view. The components may be continuous strips, or may be carried on paper backings capable of being continuously fed into an assembly device for continuous feed therethrough such that the layers are automatically aligned upon entry into the assembly device and need only be applied one on top of the other.

The electrode 1 disclosed and claimed herein has a greater surface area of electrical contact with the patient in contrast to conventional electrodes thus providing more consistent and reliable measurement. The electrode 1 does not require the use of a separately applied conductive gel at the time of attachment to the patient, nor does the electrode 1 have a self-contained supply of such gel, therefore the electrode has an extremely long shelf life with no danger of drying out, as is a problem with conventional electrodes.

Although modifications and changes may be suggested by those skilled in the art it is the intention of the inventor to embody within the patent warranted hereon all changes and modifications as reasonably and properly come within the scope of his contribution to the art.

I claim as my invention:

1. An electrode attachable to a patient for use with electronic medical monitoring or diagnostic equipment, said electrode comprising:
   a foam pad;
   a non-conductive carrier attached to one side of said of said foam pad having a conductive metallized strip thereon at a side of said carrier facing away from said foam pad;
   a conductive film strip overlying at least said conductive metallized strip, said conductive film strip extending beyond said conductive metallized strip on each side thereof and covering said carrier and a portion of said foam pad;
   an adhesive layer covering said side of said foam pad on which said non-conductive carrier is attached and also covering said conductive film strip; and
   a means for electrically connecting said conductive metallized strip to a lead of said diagnostic or monitoring equipment.

2. An electrode as claimed in claim 1 wherein said means for connecting said conductive metallized strip to said lead is a tab formed in a recess at a periphery of said foam pad onto which said conductive metallized strip extends, said conductive metallized strip being exposed on said tab.

3. An electrode as claimed in claim 1 wherein said non-conductive carrier extends beyond the conductive metallized strip.

4. An electrode for attachment to a patient for use with medical diagnostic equipment, said electrode comprising:
   a flexible backing layer;
   a non-conductive carrier layer having one side thereof adjacent said backing layer and having a conductor layer on an opposite side thereof;
   a conductive film layer overlying at least said conductor layer, said conductive film layer extending beyond said conductor layer on each side thereof and covering said carrier layer and a portion of said backing layer;
   an adhesive layer overlying said conductive film layer and a side of said backing layer to which said carrier layer is adjacent; and
   a means for electrically connecting said conductor layer to a lead of said medical diagnostic equipment.

5. An electrode as claimed in claim 4 wherein said non-conductive carrier layer is in the form of a strip.

6. An electrode as claimed in claim 4 wherein said conductor layer is in the form of a strip.

7. An electrode as claimed in claim 4 wherein said conductive film layer is in the form of a strip.

8. An electrode as claimed in claim 4 wherein said means for electrically connecting said conductor layer to a lead of said medical diagnostic equipment is a tab formed in a recess at a periphery of said backing layer onto which said conductor layer extends, said conductor layer being exposed on said tab.

9. An electrode as claimed in claim 4 wherein the nonconductive carrier layer extends beyond the conductor layer.

* * * * *

UNITED STATES PATENT AND TRADEMARK OFFICE
CERTIFICATE OF CORRECTION

PATENT NO. : 4,679,564

DATED : July 14, 1987

INVENTOR(S) : Robert W. Sessions

It is certified that error appears in the above-identified patent and that said Letters Patent is hereby corrected as shown below:

Summary of the Invention:

Column 2, line 28 - delete "discloses" and insert -- disclosed --.

Description of the Preferred Embodiments:

Column 2, line 63 - delete "faom" and insert -- foam --.

In the Claims:

Signed and Sealed this

Fourteenth Day of June, 1988

*Attest:*

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO. : 4,679,564

DATED : July 14, 1987

INVENTOR(S) : Robert W. Sessions

It is certified that error appears in the above-identified patent and that said Letters Patent is hereby corrected as shown below:

Column 3, line 55 - delete "of said"

Signed and Sealed this

Twenty-third Day of August, 1988

*Attest:*

DONALD J. QUIGG

*Attesting Officer*  *Commissioner of Patents and Trademarks*